United States Patent [19]

Chan

[11] Patent Number: 5,628,123

[45] Date of Patent: May 13, 1997

[54] ATTACHMENT FOR A HAIR DRYER

[75] Inventor: Wing-Kin Chan, Hong Kong, Hong Kong

[73] Assignee: China Pacific Trade Ltd., Virgin Islands (Br.)

[21] Appl. No.: 247,251

[22] Filed: May 23, 1994

[51] Int. Cl.⁶ .................................................. F26B 19/00
[52] U.S. Cl. ........................................ 34/90; 392/384
[58] Field of Search ............................. 34/96, 97, 98, 34/101, 282, 90, 91; 392/383, 384, 385

[56] References Cited

U.S. PATENT DOCUMENTS

| | | | |
|---|---|---|---|
| 4,230,279 | 10/1980 | Forsberg | 239/559 |
| 4,668,855 | 5/1987 | Wilson et al. | 219/370 |
| 4,759,135 | 7/1988 | Scivoletto | 34/97 |
| 4,864,735 | 9/1989 | Chung | 34/90 |
| 4,936,027 | 6/1990 | Tsuji | 34/90 |
| 4,955,145 | 9/1990 | Scivoletto | 132/271 |
| 4,972,607 | 11/1990 | Lagace | 34/90 |
| 5,488,783 | 2/1996 | Parkinson et al. | 34/98 |

*Primary Examiner*—Henry A. Bennett
*Assistant Examiner*—Gregory Wilson
*Attorney, Agent, or Firm*—Burns, Doane, Swecker & Mathis

[57] ABSTRACT

An attachment for a hair dryer is disclosed of the type that requires a source of power, for example a massaging apparatus or an infra-red radiation heater. Rather than provide the attachment with its own power source, the attachment is formed with a terminal that allows it to be connected to the power supply circuit of a suitably adapted hair dryer.

15 Claims, 6 Drawing Sheets

ATTACHMENT FOR A HAIR DRYER

FIELD OF THE INVENTION

This invention relates to an attachment for a hairdryer, for example to a massaging apparatus that may be combined with a hair dryer, or to a radiation heater mat may be attached to a hair dryer.

BACKGROUND OF THE INVENTION

It is known that a beneficial effect may be achieved by massaging the scalp. Traditionally this has been done by the manual action of a hairdresser's fingers. However this requires a visit to a hairdresser or to a beauty salon, and it is not really possible for a person to massage their own scalp very easily.

It would be desirable therefore to provide a massaging apparatus that enables a person to massage their own scalp. It would be particularly desirable to provide such a massaging apparatus that may be used in conjunction with a hair dryer whereby a massaging action can be combined with hot air.

Radiation heaters are also known and it would also be desirable to provide a radiation heater that could be combined with a hair dryer.

However both massagers and radiation heaters require a power source for their operation. Including the power source in the attachment however would increase the complexity and/or weight of the attachment. It will be appreciated that this is a disadvantage, not only for massagers or radiation heaters but for any attachment that requires a source of power, for example a mist sprayer.

SUMMARY OF THE INVENTION

According to the present invention there is provided an attachment for a hair dryer comprising, means for removably attaching the attachment to the hot air outlet of the barrel of the hair dryer, and means for electrically connecting the attachment to the power supply circuit of the hair dryer.

By means of this arrangement there is no requirement for the attachment to be provided with its own power source, instead the attachment may rely upon the power source of the hair dryer, be that a battery or mains power source.

In one embodiment the attachment may be a massaging apparatus. Preferably the massaging apparatus may comprise a plurality of massaging finger elements, and drive means for causing rotation of the massaging finger elements.

Preferably the drive means comprises an electric drive motor, the output of which drives the massaging finger elements in rotation via a gear train. In a particularly preferred arrangement the massaging finger elements may be disposed in a circular array, with each said finger element being provided with an associated gear, said gears meshing with each other whereby all the gears and hence all the finger elements may be rotatably driven together.

Since the massaging apparatus is adapted to be used in conjunction with a hair dryer, the massaging apparatus may be formed with a surrounding diffuser housing whereby in use hot air may be diffused around the massaging apparatus whereby hair may be dried while the scalp is being massaged.

In another embodiment the attachment may be an infrared radiation heater. In such an embodiment that attachment may comprise a bulb, a reflector element and a hood element.

The electrical connection means provided between the hair dryer and the attachment may be such as to provide the attachment with a source of AC or DC power. For example the massaging apparatus would require a DC supply while the radiation heater requires an AC supply. Conceivably the connection means could be configured to provide DC or AC voltage selectively.

It will also be understood that both attachments could be formed integrally with a hair dryer, and therefore the invention also extends to a hair dryer formed with a massaging unit attached to the hot air outlet of the barrel of the hair dryer, said massaging unit comprising a plurality of massaging fingers and drive means for causing rotation of the massaging finger elements.

Similarly the invention also extends to a hair dryer formed with a radiation heater attached to the hot air outlet of the barrel of the hair dryer, the radiation heater comprising a bulb, a reflector element and a hood element.

In general terms one may regard the invention as extending to a hair dryer provided with an attachment, said attachment being of a type requiring a source of power, and comprising electrical connection means whereby said attachment may be connected to the power supply circuit of the hair dryer.

BRIEF DESCRIPTION OF THE DRAWINGS

Some embodiments of the invention will now be described by way of example and with reference to the accompanying drawings, in which.

DETAILED DESCRIPTION OF PREFERRED EMBODIMENTS

Figure 1:
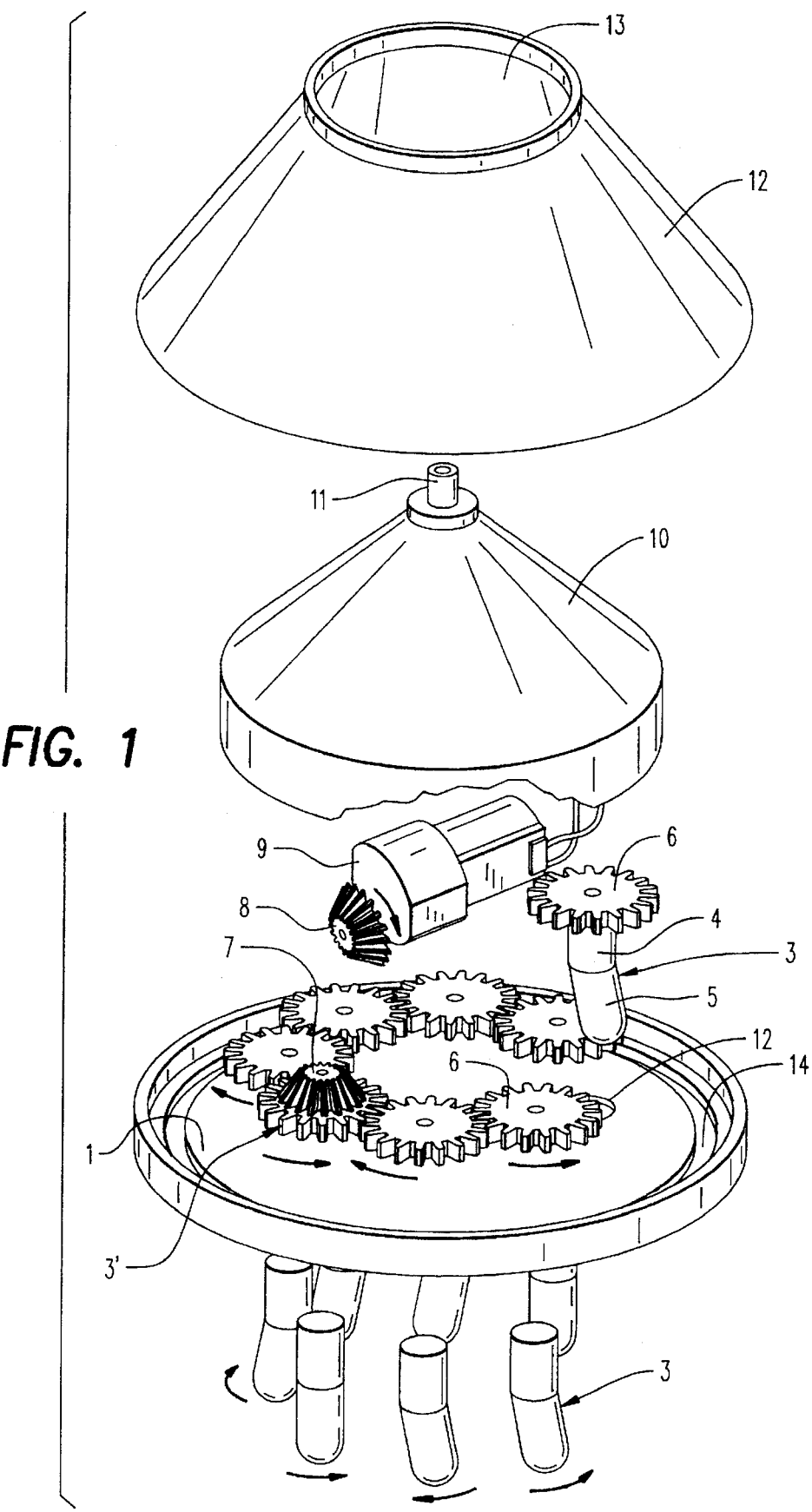
FIG. 1 is an exploded perspective view of an attachment according to a first embodiment of the invention in the form of a massaging apparatus.

Referring firstly to FIG. 1 there is shown an attachment for a hair dryer in the form of a massaging apparatus. The massaging apparatus comprises a circular base plate 1 provided with a plurality of holes 2 arranged in a circle. Located in each hole 2 is a massaging finger element 3. The massaging finger elements 3 each comprise a first shaft portion 4 of a length greater than the thickness of the plate 1, a second shaft portion 5 provided at an angle to the first shaft portion 4 and formed of a relatively soft resilient material for a massaging effect, and a drive gear 6 provided at the end of the first shaft portion remote from the second portion.

As can be seen from FIG. 1 the finger elements 3 are located in the holes 2 and are free to rotate therein. The drive gears 6 on the respective finger elements 3 whereby rotation of one finger element causes rotation of all other such elements, but with alternate finger elements rotating in opposite directions as shown by the arrows in FIG. 1. One of the finger elements 3' is also provided with a bevel gear 7 which engages a corresponding bevel gear 8 provided on the output shaft of an electric motor 9. Thus it will be understood that upon operation of the motor 9 the finger elements 3 are caused to rotate and may apply a massaging effect.

The gears and the motor are all provided within a conical gear box cover 10 at the apex of which is provided a DC connection terminal 11 whereby the motor may be connected to the power supply circuit of a hair dryer in a manner to be described further below. Surrounding the gear box cover 10 is a frusto-conical diffuser housing 12, the smaller open end 13 of which is provided with means (not shown in FIG. 1) for connecting to the hot air outlet or a hair dryer barrel. Such means may for example comprise a screw thread, or an arrangement of engaging lugs and recesses. When the attachment is fitted to a hair dryer the dryer can still be operated and hot air will pass into the diffuser housing 12 and in the gap defined between the gear box cover 10 and the diffuser housing and will exit through an annular gap 14 provided at the edge of the base plate 1. Thus hot air can be provided at the same time that the massaging fingers can be caused to rotate to massage the scalp.

Figure 2:
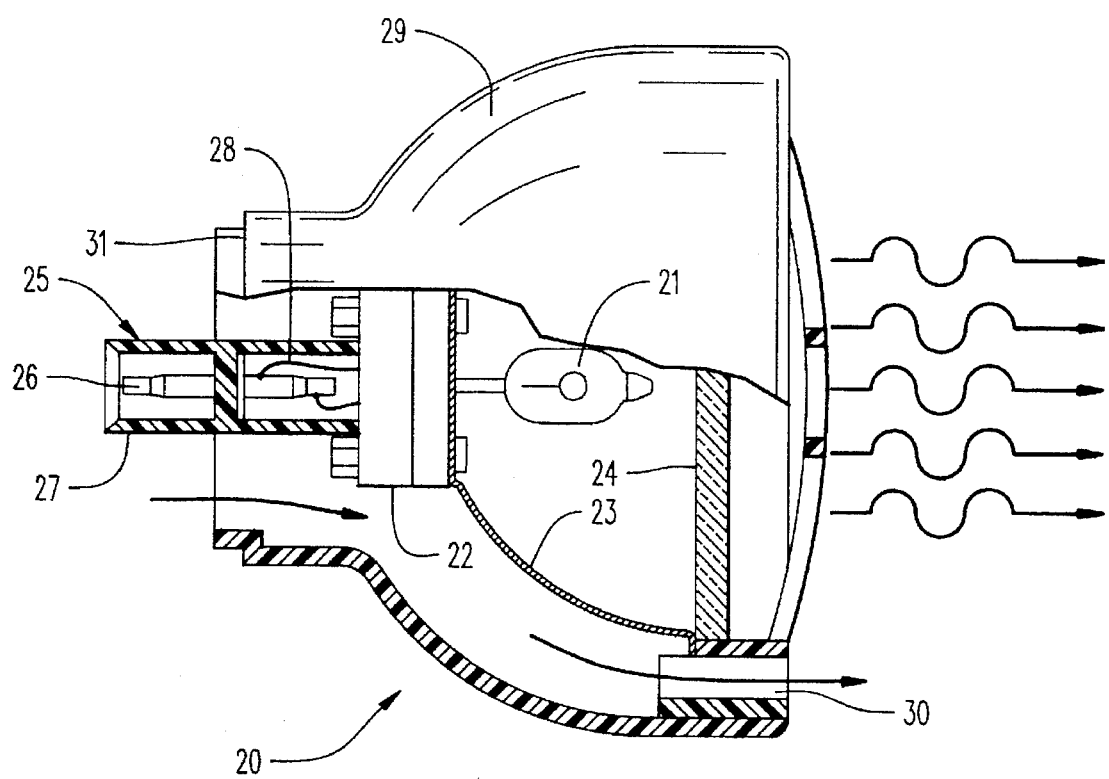
FIG. 2 is a sectional side view of an attachment according to a second embodiment of the invention in the form of a radiation heater.

Turning now to FIG. 2 there is shown therein an alternative embodiment in the form of an infra-red radiation heater 20. The heater 20 comprises a bulb 21 mounted to a base unit 22 and surrounded by an aluminium reflector 23. The bulb 21 is protected from damage by a sheet 24 of glass, plastic, crystal or the like as is conventional.

To the rear of the base unit 22 is formed an electrical connection terminal 25 of a conventional pin type. Terminal 25 comprises a pin 26 within a cylindrical sleeve 27, the sleeve and the pin being divided into two halves. The half of the pin adjacent the base unit 22 is provided with connections for leads 28 connecting to the bulb 21. The other half of the pin is adapted to be received in a corresponding socket adaptor formed on the hair dryer and to be described below with reference to FIG. 3.

It will also be noted in FIG. 2 that surrounding the reflector 23 but spaced therefrom is a diffuser housing 29 whereby hot air exiting the outlet of a hair dryer to which the attachment is fixed can pass in the space defined between the diffuser housing and the reflector 23 and can exit the attachment through an annular opening 30 surounding the radiation heater.

The neck portion 31 of the diffuser housing may be provided with a stepped shoulder portion for engaging, eg by friction, the outlet of a hair dryer. The embodiment of FIG. 1 may use a similar attachment means.

Figure 3:
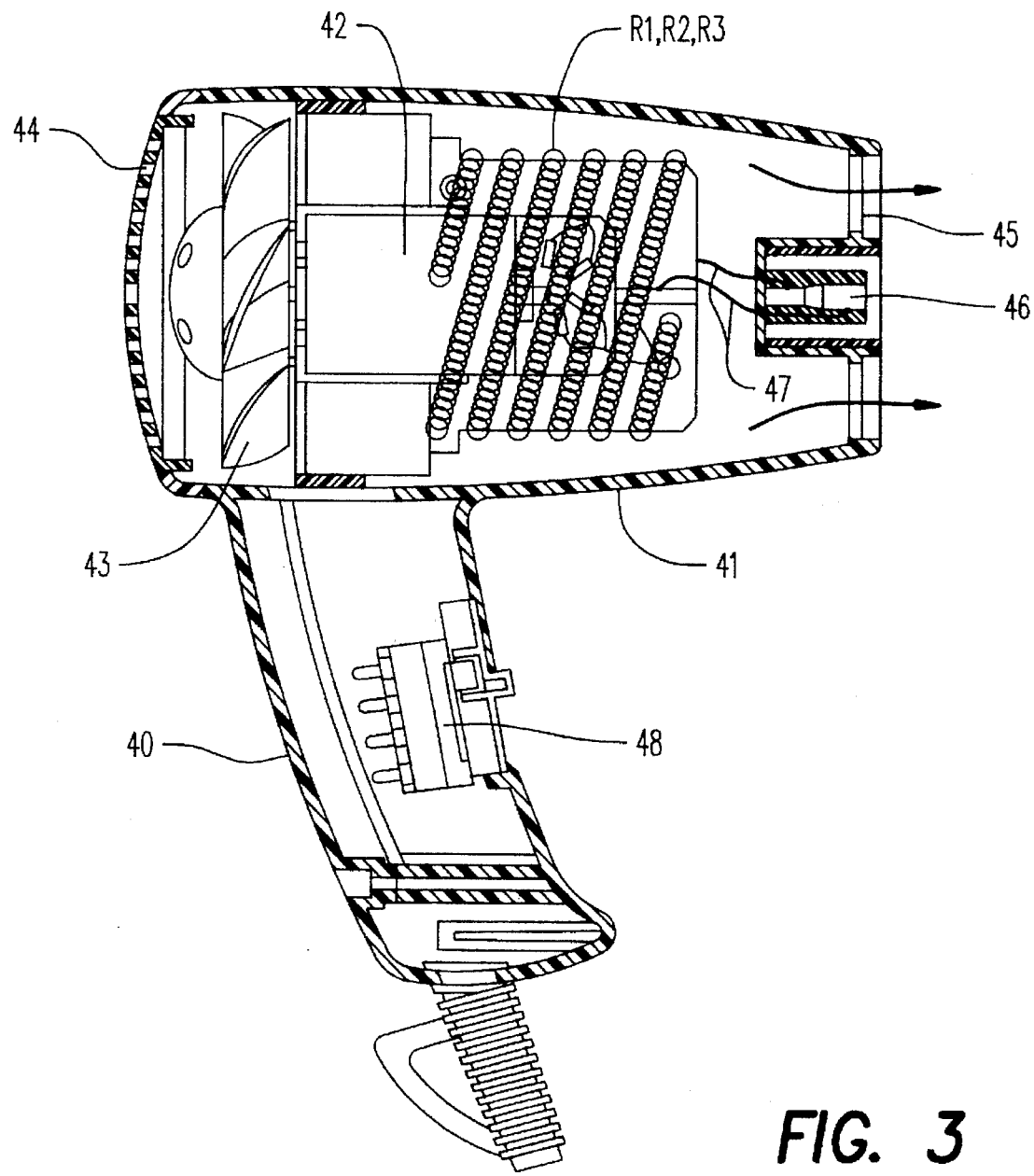
FIG. 3 is a sectional side view of a hair dryer adapted to supply an attachment with a DC voltage.

Referring to FIG. 3 the structure of a hair dryer to which such an attachment may be fixed. The basic structure of the hair dryer is conventional and comprises a handle portion 40 and a barrel portion 41. Within the barrel 41 are located a motor 42 which drives a fan 43 to draw air into the barrel through a rear grill 44, and resistive heating elements R1, R2 and R3. An on/off switch 48 is also provided.

Figure 4:
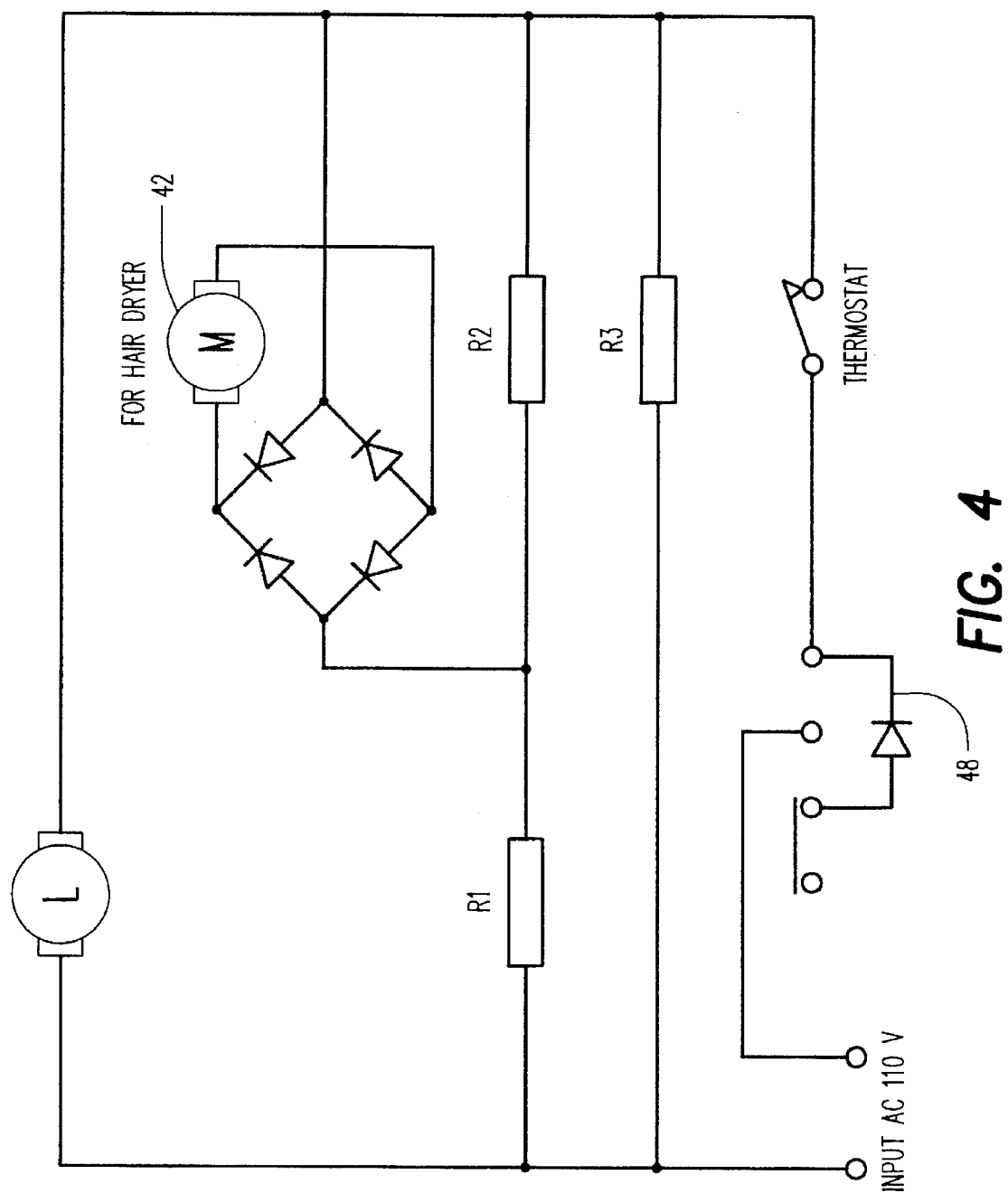
FIG. 4 shows a circuit diagram for the hair dryer of FIG. 3.

The barrel 41 is formed with an outlet grill 45 for the discharge of hot air drawn into the dryer at the rear and heated by the resistive heating elements. Centrally located in the grill 45 is a sock adaptor 46 for receiving the terminal pin 26 of the attachment. Socket adaptor 46 is connected by leads 47 to the power supply circuit of the hair dryer in the manner shown in the circuit diagram comprising FIG. 4. From FIG. 4 it will be seen that the attachment, load L, is connected in parallel across the power supply circuit so that the attachment, in this case the radiation heater, is provided with an AC supply equal to that supplied to the hair dryer itself, 110 V AC. It will also be seen that the power supply circuit is provided with an on/off switch and a protective thermostat.

Figure 5:
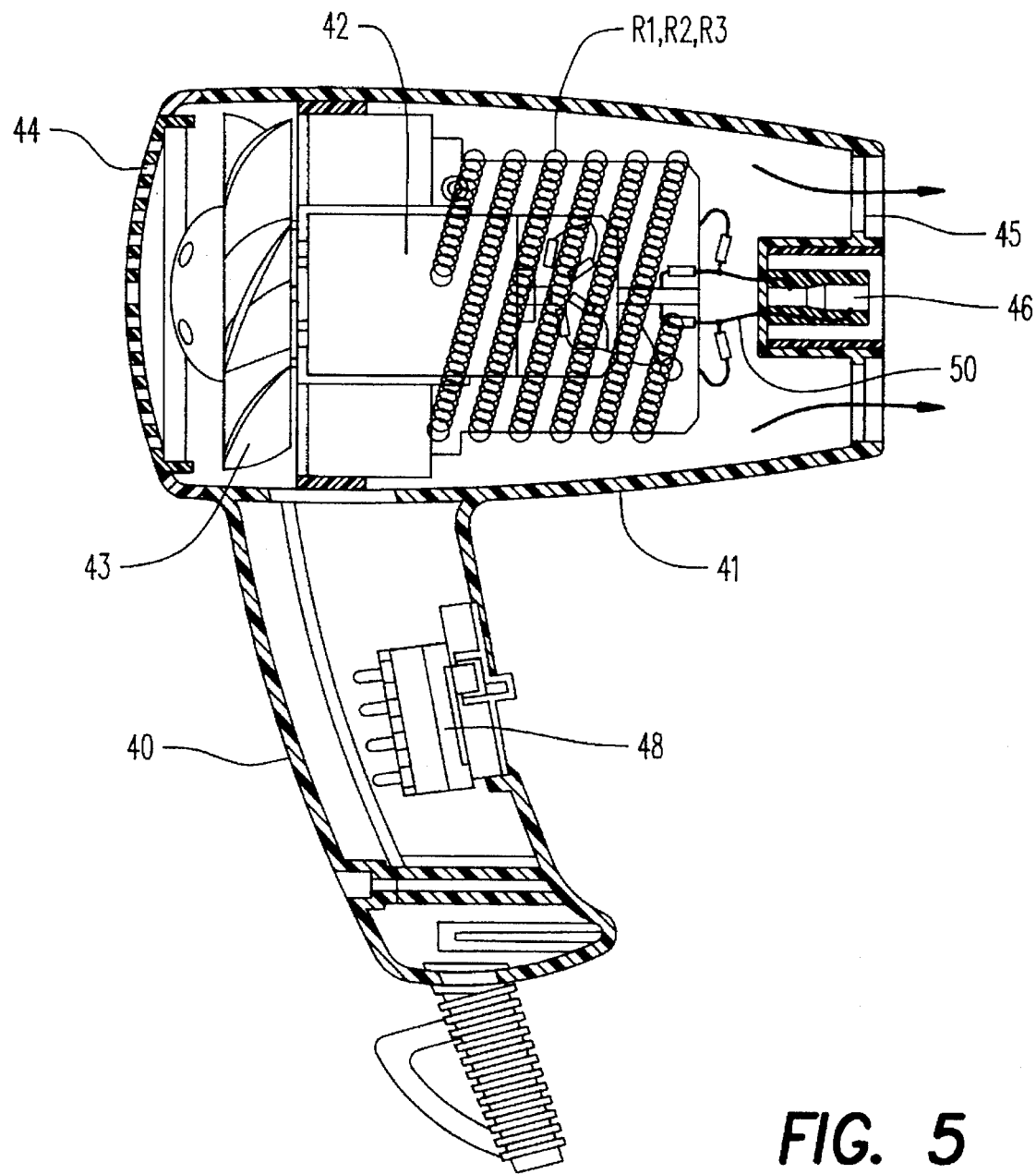
FIG. 5 is a sectional side view of a hair dryer adapted to supply an attachment with a AC voltage.
Figure 6:
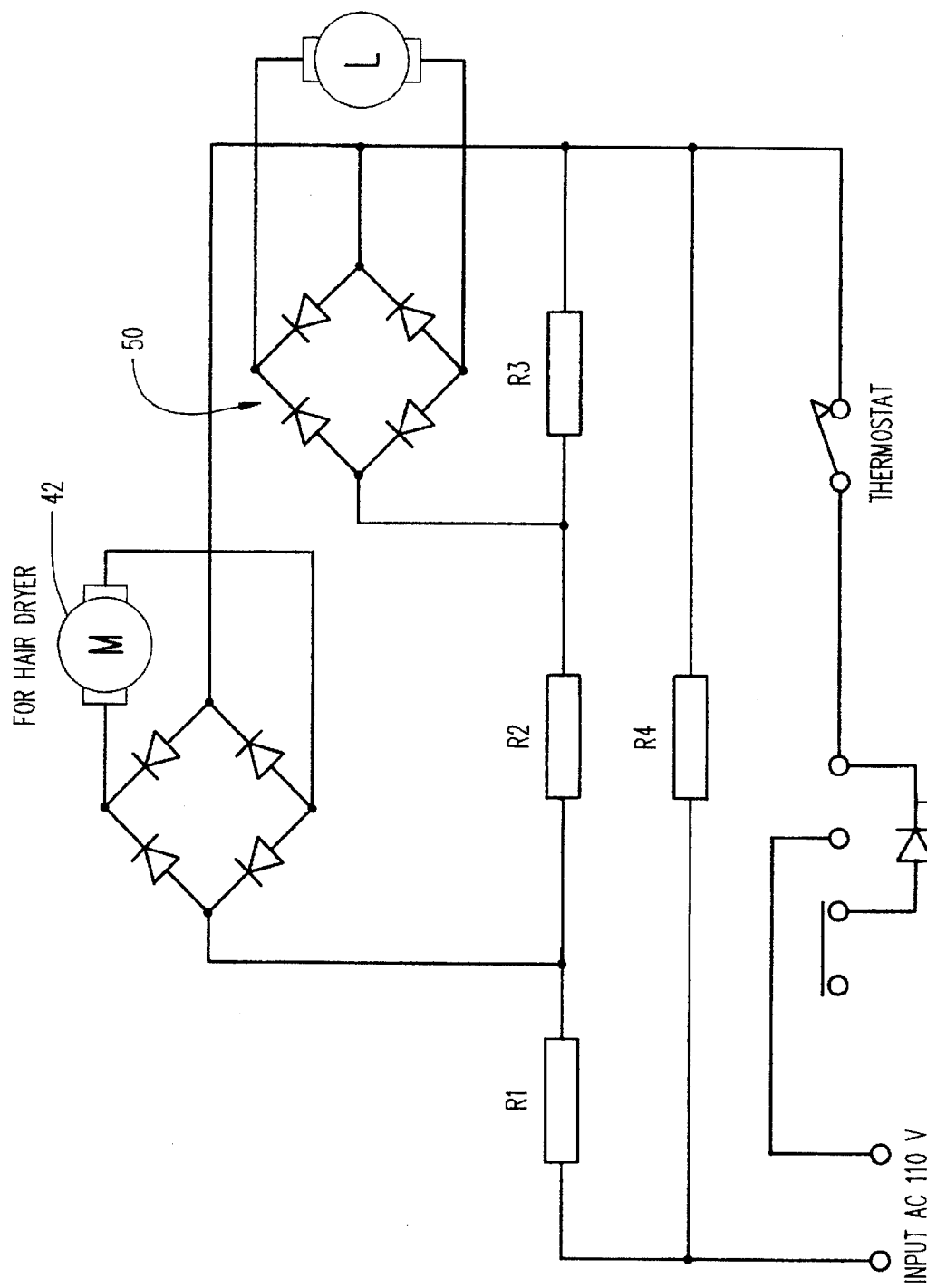
FIG. 6 shows a circuit diagram for the hair dryer of FIG. 5.

FIGS. 5 and 6 illustrate an alternative arrangement for the massaging apparatus embodiment. The motor for the massaging fingers will require only a relatively low DC voltage, and as seen in FIG. 6 this may be achieved by taking the supply for the massaging apparatus from across one of the heating resistive elements, suitably rectified by a rectifying circuit 50. In FIG. 5 the hair dryer is substantially identical to that shown in FIG. 3 subject to the addition of rectifying circuit 50.

I claim:

1. An electrically-powered attachment for a hair dryer comprising, means for removably attaching the attachment to a hot air outlet of a barrel of the hair dryer, and means for electrically connecting the attachment to a power supply circuit of the hair dryer.

2. An attachment as claimed in claim 1 wherein the attachment is a massaging apparatus.

3. An attachment as claimed in claim 2 wherein said massaging apparatus comprises a plurality of massaging finger elements, and drive means for causing rotation of the massaging finger elements.

4. An attachment as claimed in claim 3 wherein said massaging finger elements are disposed in a circular array, with each said finger element being provided with an associated gear, said gears meshing with each other whereby all the gears and hence all the finger elements may be rotatably driven together.

5. An attachment as claimed in claim 2 wherein said massaging apparatus is provided with a surrounding diffuser housing.

6. An attachment as claimed in claim 1 wherein said attachment is a radiation heater.

7. An attachment as claimed in claim 6 wherein said radiation heater comprises a bulb, a reflector element and a diffuser housing.

8. A hair dryer provided with an attachment, said attachment being of the type requiring a source of power, and having electrical connection means comprising an electrical socket located in a hot air outlet of a barrel of the hair dryer, and an electrical terminal on said attachment that is received in said socket when the attachment is attached to the hair dryer, whereby said attachment may be connected to a power supply circuit associated with the hair dryer.

9. A hair dryer as claimed in claim 8 wherein said electrical connection means is adapted to supply the attachment with a DC supply.

10. A hair dryer as claimed in claim 8 wherein said electrical connection means is adapted to supply the attachment with an AC supply.

11. The attachment of claim 1 wherein said connecting means includes an electrical terminal that is adapted to mate with an electrical socket located in a hot air outlet of the barrel of a hair dryer.

12. A hair dryer having a heat source, a hot air outlet formed on a barrel, and a fan for blowing air heated by said heat source out of said outlet, and further including a radiation heater attached to said hot air outlet, said radiation heater comprising a bulb, a reflector element and a diffuser housing for directing said heated air past said reflector element.

13. The hair dryer of claim 12 wherein said diffuser housing forms an annular opening which surrounds the bulb and reflector element.

14. The hair dryer of claim 12 including means within said hair dryer for providing electrical power to said heat source and said fan, and wherein said radiation heater comprises an attachment that is separable from said barrel, and further including an electrical connector for connecting said bulb to said power providing means when said radiation heater is attached to said barrel.

15. The hair dryer of claim 14 wherein said electrical connector comprises an electrical socket located in said hot air outlet and connected to said power providing means, and an electrical terminal connected to said bulb, which is received within said socket when said radiation heater is attached to said barrel.

* * * * *